(12) United States Patent
Scheller et al.

(10) Patent No.: US 8,197,468 B2
(45) Date of Patent: Jun. 12, 2012

(54) SURGICAL INSTRUMENT HANDLE WITH ADJUSTABLE ACTUATOR POSITION

(75) Inventors: Gregg D. Scheller, Glencoe, MO (US); Michael D. Auld, Coral Springs, FL (US)

(73) Assignee: Synergetics, Inc., St. Charles, MO (US)

( * ) Notice: Subject to any disclaimer, the term of this patent is extended or adjusted under 35 U.S.C. 154(b) by 754 days.

(21) Appl. No.: 10/586,018

(22) PCT Filed: Nov. 15, 2004

(86) PCT No.: PCT/US2004/038175
§ 371 (c)(1),
(2), (4) Date: Oct. 26, 2006

(87) PCT Pub. No.: WO2005/048849
PCT Pub. Date: Jun. 2, 2005

(65) Prior Publication Data
US 2007/0179475 A1    Aug. 2, 2007

(51) Int. Cl.
*A61B 17/00* (2006.01)
*A61B 17/70* (2006.01)
(52) U.S. Cl. ............... 606/1; 606/264; 606/265
(58) Field of Classification Search ............. 606/1, 100, 606/182, 265; 604/265
See application file for complete search history.

(56) References Cited

U.S. PATENT DOCUMENTS

| | | | |
|---|---|---|---|
| 4,760,848 A | 8/1988 | Hasson | |
| 5,211,652 A | 5/1993 | Derbyshire | |
| 5,275,607 A | 1/1994 | Lo et al. | |
| 5,290,302 A | 3/1994 | Pericic | |
| 5,338,317 A | 8/1994 | Hasson et al. | |
| 5,370,658 A * | 12/1994 | Scheller et al. | 606/205 |
| 5,634,918 A | 6/1997 | Richards | |
| 5,827,291 A | 10/1998 | Fucci et al. | |
| 5,830,231 A | 11/1998 | Geiges, Jr. | |
| 5,893,873 A | 4/1999 | Rader et al. | |
| 5,908,426 A | 6/1999 | Pierce | |
| 5,928,263 A * | 7/1999 | Hoogeboom | 606/206 |
| 5,984,865 A | 11/1999 | Farley et al. | |

(Continued)

FOREIGN PATENT DOCUMENTS
GB          2091624 A       8/1982

*Primary Examiner* — Anhtuan Nguyen
*Assistant Examiner* — Ryan Henderson
(74) *Attorney, Agent, or Firm* — Joseph M. Rolnicki; Evans & Dixon, LLC

(57) ABSTRACT

A surgical instrument handle is removably attachable to a surgical instrument head for operation of a microsurgical instrument on the head by manipulation of the instrument handle. The instrument handle has an elongate center rod with a piston mounted on the rod for reciprocating movement. The piston engages with a piston in the attached surgical instrument head for operation of the microsurgical instrument of the head. A tapered ring is mounted on the rod and engages with the piston for reciprocating the piston. A plurality of resilient arms extend along the length of the rod and engage against a sliding surface of the ring. The plurality of resilient arms are alternatively squeezed radially inwardly by the surgeon's hand and released by the surgeon's hand to allow the resilient arms to flex radially outwardly. The inward and outward movement of the plurality of arms reciprocates the piston on the handle rod to cause operation of the surgical instrument head. The radial position of the resilient arms relative to the handle is adjustable as desired by the surgeon.

14 Claims, 2 Drawing Sheets

U.S. PATENT DOCUMENTS

| | | |
|---|---|---|
| 6,391,046 B1 | 5/2002 | Overaker et al. |
| 6,482,198 B1 | 11/2002 | Overaker et al. |
| 6,488,695 B1 * | 12/2002 | Hickingbotham ............ 606/206 |
| 6,855,126 B2 * | 2/2005 | Flinchbaugh ................. 604/265 |
| 6,855,156 B2 | 2/2005 | Etter et al. |
| 2006/0089661 A1 | 4/2006 | Dodge et al. |

* cited by examiner

SURGICAL INSTRUMENT HANDLE WITH ADJUSTABLE ACTUATOR POSITION

BRIEF DESCRIPTION OF THE DRAWINGS

Features of the invention are set forth in the following detailed description of the preferred embodiment of the invention and in the following drawing figures wherein.

DETAILED DESCRIPTION OF THE PREFERRED EMBODIMENT

Figure 1:
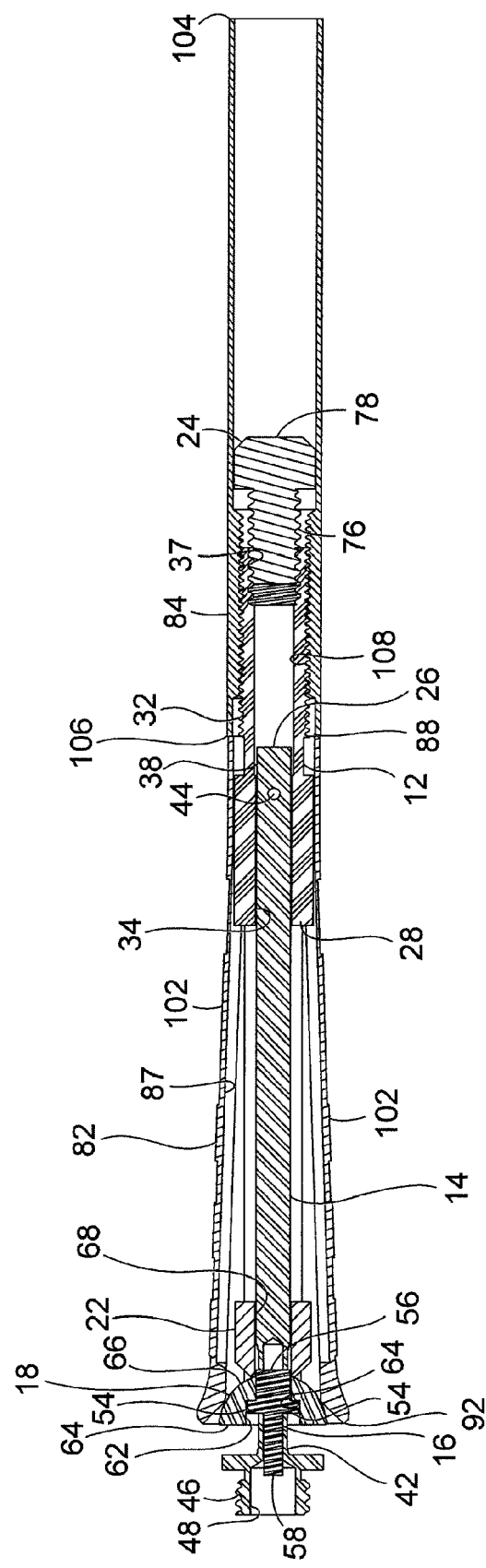
FIG. 1 is a cross section of the instrument handle of the invention.
Figure 2:
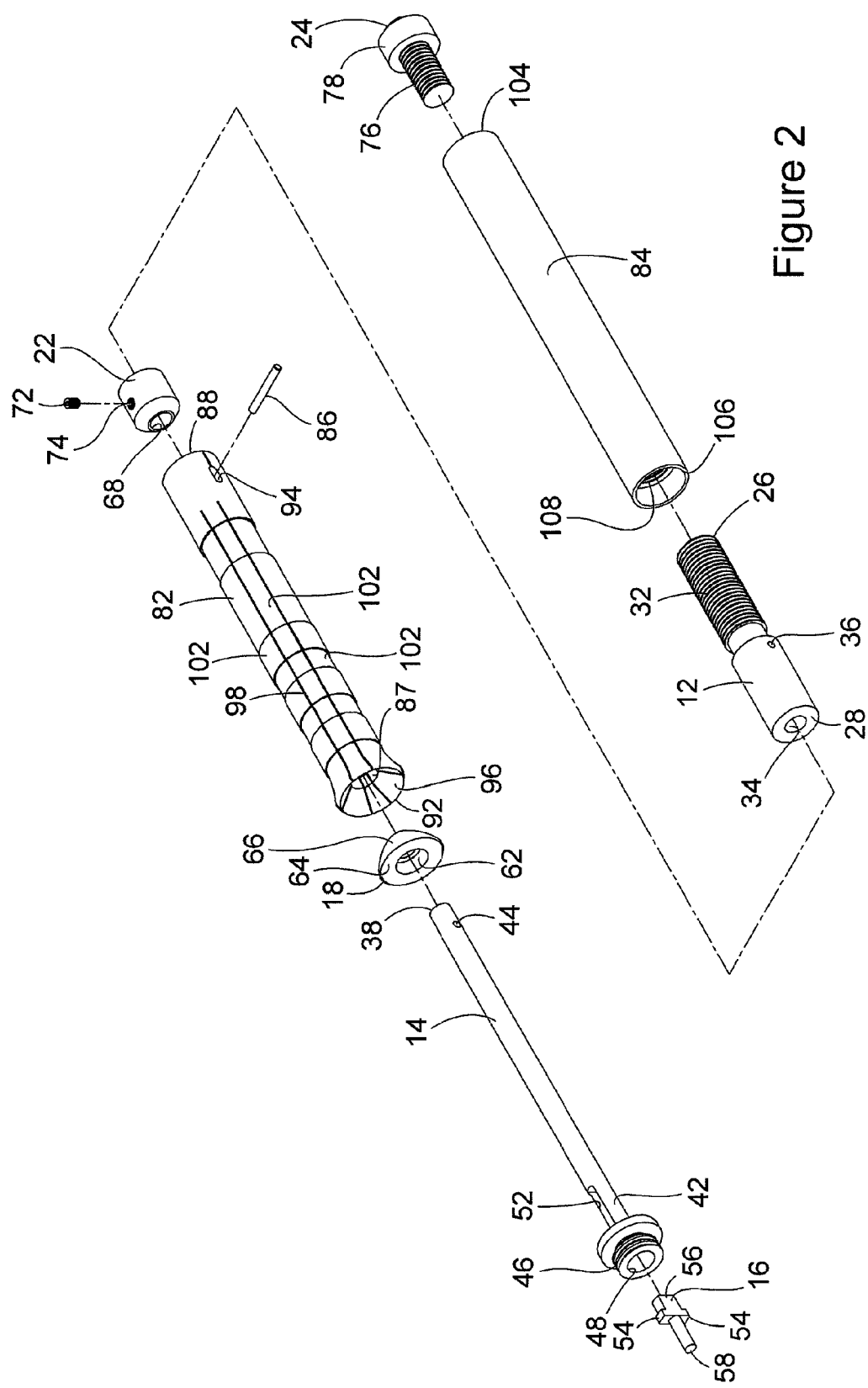
FIG. 2 is a view of the disassembled component parts of the instrument handle of the invention.

The surgical instrument handle of the invention is employed with microsurgical instrument heads of the type disclosed in the U.S. Pat. No. 5,370,658 Scheller et al. and the U.S. Pat. No. 5,893,877 Gampp, Jr. et al. both of which are incorporated herein by reference. The surgical instrument heads disclosed in these patents have surgical instruments at their distal ends that are actuated in response to reciprocating movement of head pistons at their proximal ends. The instrument handle of the invention is designed to be attached to surgical instrument heads of the type disclosed in the above referenced patents to actuate the surgical instruments of the instrument heads.

The instrument handle of the invention is manually actuated in a manner to be described, to move a piston on the instrument handle that in turn moves the head piston of the surgical instrument head attached to the handle. In this way, the instrument handle of the invention actuates the surgical instrument head of the type described in the above referenced patents. In operation of the instrument handle of the invention, the handle piston is moved against a spring-biased piston of the instrument head to produce a first stage of movement in the surgical instrument at the distal end of the instrument head. The bias on the instrument head piston against the piston of the instrument handle causes the surgical instrument at the instrument head distal end to move from its first stage of movement to its second stage of movement.

The surgical instrument handle of the invention is basically comprised of an interior assembly and an exterior assembly. The interior assembly includes a cylindrical base 12, an elongate rod 14, a piston 16, a ring 18, a piston stop 22, and a rear cap 24.

The cylindrical base 12 has a center axis with opposite proximal 26 and distal 28 ends. External screw threading 32 is provided on the exterior of the base adjacent the base proximal end 26. A center bore 34 extends through the base. A pinhole 36 extends transversely through the base and intersects the center bore 34. Internal screw threading 37 is provided in the center bore 34 adjacent the base proximal end 26.

The elongate rod 14 has a center axis and opposite proximal 38 and distal 42 ends. A pinhole 44 extends transversely through the rod proximal end 38. A surgical instrument head connector 46 having external screw threading is provided at the rod distal end 42. The instrument connector 46 has an axial center bore 48. A piston slot 52 extends transversely through the rod 14 and extends axially along the rod for a short distance adjacent the instrument connector 46. The slot 52 intersects the instrument connector center bore 48.

The piston 16 is received in the rod slot 52 for reciprocating axial movement of the piston through the rod slot. The piston 16 has a pair of transversely extending shoulders 54 intermediate the opposite proximal 56 and distal 58 ends of the piston. The piston distal end 58 projects from the pair of shoulders 54 through the center bore 48 of the rod instrument connector 46.

The ring 18 is mounted on the rod 14 for axial sliding movement of the ring. The ring has an annular cavity 62 recessed into a distal end face 64 of the ring. The annular cavity 62 receives the piston shoulders 54 to operatively connect the piston 16 with the ring 18. A proximal end face 66 of the ring 18 is formed as a conical sliding surface.

The piston stop 22 is cylindrical and has a center bore 68 that receives the elongate rod 14. The piston stop 22 is positioned adjacent the slot 52 in the rod distal end. A set screw 72 is received in an internally threaded hole 74 in the side of the piston stop 22 and engages with the elongate rod 14 to secure the piston stop in a desired position on the rod. The position of the piston stop 22 on the rod 14 limits the movement of the piston 16 toward the rod proximal end 38.

The rear cap 24 is provided with an externally threaded shank 76 and a cylindrical head 78. The screw threads on the rear cap shank 76 are screwed into the internal screw threading 37 at the base proximal end 26 closing the hollow interior of the base at its proximal end.

The exterior assembly of the surgical instrument handle is comprised of a tubular forward grip member 82, a tubular rearward grip member 84, and a pin 86. The forward grip member 82 has a center bore 87 with a center axis extending through the length of the grip member. The bore 87 extends from a proximal end 88 to a distal end 92 of the grip member. A pair of diametrically opposed elongate slots 94 are formed transversely through the forward grip member 82 adjacent the proximal end 88. The slots 94 extend axially along a portion of the length of the forward grip member adjacent the proximal end 88. A portion of the forward grip member interior bore surface 96 tapers radially outwardly as it extends from the interior bore to the forward grip member distal end 92. A plurality of axially extending slots 98 are formed in the forward grip member 82 at the forward grip member distal end 92. The axial slots 98 extend along the length of the forward grip member 82 from the distal end 92, but end short of the forward grip member proximal end 88. The axial slots 98 form a plurality of resilient arms 102 that are circumferentially arranged around the interior bore 87 of the forward grip member.

The rearward grip member 84 is a cylindrical tube having opposite proximal 104 and distal 106 ends. The exterior surface of the rearward grip member 84 is smooth. Internal screw threading 108 is provided inside the rearward grip member 84 adjacent the distal end 106. The internal screw threading 108 is complementary to the external screw threading 32 of the base 12.

The surgical instrument handle is assembled by first positioning the piston 16 in the slot 52 at the rod distal end 42. The ring 18 is then positioned over the rod and the piston shoulders 54 are received in the ring annular cavity 62. The piston stop 22 is then positioned over the rod adjacent the slot 52. The piston stop 22 is secured in its desired position adjacent the slot 52 by tightening the set screw 72 in the set screw hole 74 of the stop. The elongate rod proximal end 38 is then inserted into the base center bore 34 at the base distal end 28. The pinhole 44 of the rod is aligned with the pinhole 36 of the base.

The exterior assembly of the instrument handle is then assembled onto the interior assembly. The forward grip member 82 is positioned over the elongate rod 14 and over the proximal end 26 of the base 12. The pin slots 94 of the forward grip member 82 are aligned with the base pinhole 36 and the rod pinhole 44 and the pin 86 is inserted through the aligned holes and slots. This secures the rod 14 to the base 12, and mounts the forward grip member 82 to the rod and base for limited axial movement of the forward grip member 82 relative to the rod 14 and base 12.

The rearward grip member 84 is then mounted to the base 12 by screw threading the internal screw threads 108 at the distal end 106 of the rearward grip member onto the external screw threads 32 of the base. The rearward grip member 84 is screw threaded onto the base 12 until the distal end 106 of the rearward grip member 84 engages against the proximal end 88 of the forward grip member 82. The rear cap 24 is then screw threaded into the internal screw threading 37 at the base proximal end 26. The head 78 of the rear cap prevents the rearward grip member 84 from being removed from the instrument handle by screw threading the rearward grip member 84 off of the base 12.

With the instrument assembled as shown in FIG. 1, it should be appreciated that manually compressing the distal ends 92 of the forward grip member 82 will exert a compressive force on the conical sliding surface 66 of the ring 18. This will cause the ring 18 to move axially toward the rod distal end 42. This in turn causes the piston 16 to move through the piston slot 52 toward the rod distal end 42. This movement of the piston will actuate the surgical instrument of a surgical instrument head of the type described in the earlier referenced U.S. patents.

Releasing the manual compressive force on the distal end 92 of the forward grip member 82 will allow the piston 16 to move toward the rod proximal end 38 in response to the biasing force of the surgical instrument head attached to the instrument handle. This also results in movement of the ring 18 toward the rod proximal end 38. As the ring 18 moves the ring proximal end face 66 pulses the forward grip member distal ends 92 back to their original positions.

The novel construction of the instrument handle of the invention enables the radial spacing between the distal ends 92 of the forward grip member arms 102 to be adjusted to the desired comfort of the user. Turning the rearward grip member 84 in a first, clockwise direction relative to the forward grip member 82 will cause the forward grip member 82 to move axially along the rod 14. The movement of the forward grip member 82 is determined by the length of the axial slots 94 in the forward grip member 82. Movement of the forward grip member distal end 92 toward the rod distal end 42 will cause the distal ends 92 of the forward grip member arms 102 to expand radially outwardly as they slide over the ring proximal end surface 66. Thus, this adjustably increases the radial spacing between diametrically opposite distal ends 92 of the forward grip member arms 102. Rotating the rearward grip member 84 in a second, counterclockwise direction relative to the forward grip member 82 will allow the forward grip member 82 to move axially toward the proximal end 38 of the rod 14. This allows the distal ends 92 of the forward grip member arms 102 to slide radially inwardly, over the ring proximal end surface 66. This reduces the radial spacing between diametrically opposite distal ends 92 of the forward grip member arms 102.

Thus, in the manner discussed above, the instrument handle of the invention enables radially adjusting the width of the operative portion of the instrument handle adjacent the forward grip member distal ends 92 to suit the comfort of the user.

Although a specific embodiment of the invention has been described above, it should be understood that other modifications and variations may be made to the invention without departing from the intended scope of protection provided by the following claims.

What is claimed is:

1. A surgical instrument handle comprising:
an elongate rod having a center axis that defines mutually perpendicular axial and radial directions, the rod having a length with axially opposite proximal and distal ends; the rod distal end being adapted to be attached to a surgical instrument head;
a piston mounted on the rod adjacent the rod distal end wherein the piston is adapted to have axially reciprocating movement toward and away from the rod distal end;
a forward grip member mounted on the rod wherein the forward grip member is adapted to have axial movement between first and second positions of the forward grip member relative to the rod, the forward grip member having a plurality of resilient arms that extend along the rod, the plurality of arms having distal ends that operatively engage with the piston whereby manual movement of the arm distal ends radially inwardly moves the piston axially toward the rod distal end and movement of the piston axially away from the rod distal end moves the arm distal ends radially outwardly, there being a first radial spacing between the arm distal ends when the forward grip member is in the first position relative to the rod, and there being a second radial spacing between the arm distal ends when the forward grip member is in the second position relative to the rod, the second radial spacing being larger than the first radial spacing.

2. A surgical instrument handle that is removably attachable to a surgical instrument head, the surgical instrument handle comprising:
a cylindrical base having a length with opposite proximal and distal ends, the base proximal end having external and internal screw threading;
an elongate rod having opposite proximal and distal ends, the rod proximal end being secured to the base distal end, the rod distal end having a connector adapted for removably attaching a surgical instrument head to the connector, the connector having a center bore through the connector, and the rod distal end having a slot through the rod distal end adjacent the connector;
a piston received in the slot at the rod distal end wherein the piston is adapted to have reciprocating movement of the piston in the slot, the piston having a proximal end positioned in the slot and the piston having a distal end that projects through the connector center bore;
a ring mounted on the rod for sliding movement of the ring over the rod, the ring engaging with the piston proximal end;
a piston stop mounted on the rod in a position on the rod where the piston stop will engage with the ring and prevent further sliding of the ring toward the rod proximal end;
a forward grip member mounted on the base distal end wherein the forward grip is adapted to have limited reciprocating movement of the forward grip member on the base distal end, the forward grip member having a plurality of resilient arms that are circumferentially arranged around the rod and project from the base along the rod, the plurality of resilient arms having distal ends, the distal ends of the resilient arms engaging with the ring; and,
a rearward grip member having an interior bore with internal screw threading that mates with the external screw threading of the base, whereby turning the rearward grip member in a first direction causes the rearward grip member to move toward the rod distal end and push the forward grip member to move toward the rod distal end and causes the distal ends of the forward grip member resilient arms to move over the ring and move circumferentially outwardly away from the rod, and turning the rearward grip member in a second direction causes the rearward grip member to move away from the rod distal end and allows the distal ends of the resilient arms to move over the ring and move circumferentially inwardly toward the rod pushing the forward grip member to move away from the rod distal end.

3. A surgical instrument handle comprising:
an elongate rod having a center axis that defines mutually perpendicular axial and radial directions, the rod having a length with axially opposite proximal and distal ends; the rod distal end being adapted to be attached to a surgical instrument head;
a piston mounted on the rod adjacent the rod distal end wherein the piston is adapted to have axially reciprocating movement of the piston toward and away from the rod distal end;
a forward grip member operatively connected with the rod wherein the forward grip member is adapted to have axial movement between first and second positions of the forward grip member relative to the rod;
a plurality of resilient arms integrally connected with the forward grip member and operatively connected with the piston whereby manual movement of the arms radially inwardly moves the piston axially toward the rod distal end, and movement of the piston axially away from the rod distal end moves the arms radially outwardly, there being a first radial spacing between the arms when the forward grip member is in the first position relative to the rod, and there being a second radial spacing between the arms when the forward grip member is in the second position relative to the rod, the second radial spacing being larger than the first radial spacing.

4. The handle of claim 3, further comprising:
the plurality of arms extending from the forward grip member along the rod, the plurality of arms having distal ends that operatively engage with the piston, the axial movement of the forward grip member relative to the rod moving the distal ends of the arms relative to the rod.

5. The handle of claim 4, further comprising:
the plurality of arms being circumferentially arranged around the rod and the piston.

6. The handle of claim 4, further comprising:
a rearward grip member operatively connected to the rod wherein the rearward grip member is adapted to have movement of the rearward grip member toward the rod distal end and away from the rod distal end, the rearward grip member being operatively connected with the forward grip member to cause the axial movement of the forward grip member relative to the rod in response to the movement of the rearward grip member toward and away from the rod distal end.

7. The handle of claim 3, further comprising:
the rod distal end having a connector that attaches the rod to a surgical instrument head.

8. The handle of claim 7, further comprising:
the rod connector being adapted for removably attaching the surgical instrument head to the connector.

9. The handle of claim 7, further comprising:
the connector having a center bore through the connector; and,
the piston having opposite proximal and distal ends, the piston distal end extending through the connector center bore.

10. The handle of claim 9, further comprising:
the rod distal end having a slot adjacent the connector; and
the piston proximal end being positioned in the slot wherein the piston proximal end is adapted to have reciprocating movement of the piston proximal end in the slot and reciprocating movement of the piston distal end in the connector bore.

11. A surgical instrument handle comprising:
an elongate rod having a center axis that defines mutually perpendicular axial and radial directions, the rod having a length with axially opposite proximal and distal ends; the rod distal end being adapted to be attached to a surgical instrument head;
a piston mounted on the rod adjacent the rod distal end wherein the piston is adapted for axially reciprocating movement of the piston toward and away from the rod distal end;
a forward grip member operatively connected with the rod wherein the forward grip member is adapted for axial movement between first and second positions of the forward grip member relative to the rod;
a plurality of resilient arms operatively connected with the forward grip member and operatively connected with the piston whereby manual movement of the arms radially inwardly moves the piston axially toward the rod distal end, and movement of the piston axially away from the rod distal end moves the arms radially outwardly, there being a first radial spacing between the arms when the forward grip member is in the first position relative to the rod, and there being a second radial spacing between the arms when the forward grip member is in the second position relative to the rod, the second radial spacing being larger than the first radial spacing; and,
a ring mounted on the rod wherein the ring is adapted to have reciprocating movement of the ring toward the rod proximal end and toward the rod distal end, the ring engaging with the piston.

12. The handle of claim 11, further comprising:
the ring having a sliding surface; and,
the plurality of resilient arms engaging with the ring sliding surface for sliding movement of the arms on the sliding surface when the ring moves toward the rod proximal end and when the ring moves toward the rod distal end, the plurality of resilient arms moving between the first radial spacing between the arms and the second radial spacing between the arms in response to the sliding movement of the arms on the ring sliding surface.

13. The handle of claim 11, further comprising:
the plurality of arms extending from the forward grip member along the rod, the plurality of arms having distal ends that engage with the ring, the axial movement of the forward grip member relative to the rod moving the distal ends of the arms relative to the rod and the ring.

14. The handle of claim 13, further comprising:
a rearward grip member operatively connected to the rod for movement of the rearward grip member toward the rod distal end and away from the rod distal end, the rearward grip member being operatively connected with the forward grip member to cause the axial movement of the forward grip member relative to the rod in response to the movement of the rearward grip member toward the rod distal end and away from the rod distal end.

* * * * *